United States Patent [19]
Tollefson

[11] Patent Number: 5,958,921
[45] Date of Patent: Sep. 28, 1999

[54] METHOD FOR TREATING DEPRESSION WITH OLANZAPINE

[75] Inventor: Gary D Tollefson, Indianapolis, Ind.

[73] Assignee: Eli Lilly and Company, Indianapolis, Ind.

[21] Appl. No.: 09/091,539

[22] PCT Filed: Dec. 4, 1996

[86] PCT No.: PCT/US96/19574

§ 371 Date: Jun. 18, 1998

§ 102(e) Date: Jun. 18, 1998

[87] PCT Pub. No.: WO97/23220

PCT Pub. Date: Jul. 3, 1997

Related U.S. Application Data

[60] Provisional application No. 60/009,173, Dec. 22, 1995.

[51] Int. Cl.$^6$ .................................................. A61K 31/55
[52] U.S. Cl. ............................................................ 514/220
[58] Field of Search ............................................. 514/220

[56] References Cited

U.S. PATENT DOCUMENTS 5,229,382  7/1993  Chakrabarti et al. .
5,605,897  2/1997  Beasley, Jr. et al. .................... 514/220

*Primary Examiner*—William R. A. Jarvis
*Attorney, Agent, or Firm*—Arleen Palmberg

[57] ABSTRACT

This invention relates to the use of the antipsychotic drug olanzapine for the treatment of depression, including depressive signs and symptoms and Major Depression.

13 Claims, No Drawings

METHOD FOR TREATING DEPRESSION WITH OLANZAPINE

This application is a 371 of PCT/US96/19574, filed Dec. 4, 1996 and claims priority to provisional application Ser. No. 60/009,173, filed Dec. 22, 1995.

This invention relates to a method for treating depression using 2-methyl-4-(4-methyl-1-piperazinyl)-10H-thieno[2,3-b][1,5]benzodiazepine.

Major Depressive Disorder is associated with a high mortality. Up to 15% of individuals with severe Major Depressive Disorder die by suicide. Epidemiological evidence also suggests that there is a fourfold increase in death rates in individuals with Major Depressive Disorder who are over age 55 years. Individuals admitted to nursing homes with Major Depressive Disorder have a markedly increased likelihood of death in the first year.

Depression is a prevalent condition. The lifetime risk for Major Depressive Disorder in community samples has varied from 10% to 25% for women and 5% to 12% for men. The prevalence of Major Depressive Disorder appear to be unrelated to ethnicity, education, income, or marital status.

The 2-methyl-4-(4-methyl-1-piperazinyl)-10H-thieno[2,3-b][1,5]benzodiazepine compound is described in U.S. Pat. No. 5,229,382 ('382), herein incorporated by reference in its entirety.

The presently claimed invention provides a method for treating depressive signs and symptoms comprising administering an effective amount of a 2-methyl-4-(4-methyl-1-piperazinyl)-10H-thieno[2,3-b][1,5]benzodiazepine compound to a patient in need thereof.

Additionally, the present invention provides a method for treating major depression comprising administering an effective amount of a 2-methyl-4-(4-methyl-1-piperazinyl)-10H-thieno[2,3-b][1,5]benzodiazepine compound to a patient in need thereof.

2-Methyl-4-(4-methyl-1-piperazinyl)-10H-thieno[2,3-b][1,5]benzodiazepine, is a compound of Formula(I):

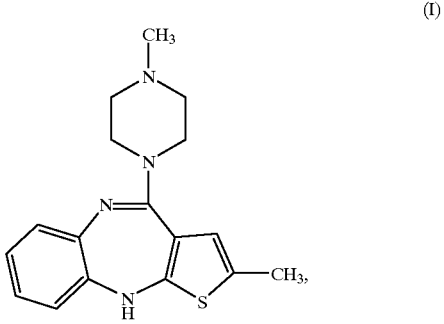

and is described in the '382 patent. The '382 patent teaches that 2-methyl-4-(4-methyl-1-piperazinyl)-10H-thieno[2,3-b][1,5]benzodiazepine can be useful for the treatment of psychotic conditions and mild anxiety states.

Surprisingly, and in accordance with the present invention, Applicants have discovered that 2-methyl-4-(4-methyl-1-piperazinyl)-10H-thieno[2,3-b][1,5]benzodiazepine can be useful for treating depressive signs and symptoms.

The usefulness of 2-Methyl-4-(4-methyl-1-piperazinyl)-10H-thieno[2,3-b][1,5]benzodiazepine for treating depressive signs and symptoms can be demonstrated by clinical trial.

Such effectiveness for the treatment, amelioration and/or prevention of depressive signs and symptoms was shown in the following clinical trial:

The study was an international double-blind, parallel trial conducted in one thousand nine hundred ninety six (1,996) subjects. Individuals were randomized 2:1 to either 2-Methyl-4-(4-methyl-1-piperazinyl)-10H-thieno[2,3-b][1,5]benzodiazepine or haloperidol (5 to 20 mg per day) for six weeks. Subjects were evaluated weekly using the MADRS standardized assessment tool. Depressive signs and symptoms were related to suicidality.

2-Methyl-4-(4-methyl-1-piperazinyl)-10H-thieno[2,3-b][1,5]benzodiazepine was statistically significantly better than haloperidol in baseline endpoint MADRS total score change. A statistically significant number of subjects in the haloperidol treatment group demonstrated a worsening of depressive signs and symptoms.

2-Methyl-4-(4-methyl-1-piperazinyl)-10H-thieno[2,3-b][1,5]benzodiazepine is effective over a wide dosage range, the actual dose administered being dependent on the condition being treated. For example, in the treatment of adult humans, dosages of from about 1 to 40 mg, and most preferably 5 to 30 mg per day may be used. A once a day dosage is normally sufficient, although divided doses may be administered. For treatment of depressive signs and symptoms in a human, a dose range of from about 2.5 to 30 mg, preferably 5 to 25 mg per day is suitable. Radiolabelled 2-Methyl-4-(4-methyl-1-piperazinyl)-10H-thieno[2,3-b][1,5]benzodiazepine, can be detected in the saliva and thus the compound can potentially be monitored in patients to assess compliance.

The 2-methyl-4-(4-methyl-1-piperazinyl)-10H-thieno[2,3-b][1,5]benzodiazepine compound will normally be administered orally for the treatment of depressive signs and symptoms, or may be administered by injection and, for this purpose, it is usually employed in the form of a pharmaceutical composition. Other suitable formulations are taught in the '382 patent.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

For the treatment of depressive signs and symptoms, the patient may be a non-human mammal. In such instances, the 2-methyl-4-(4-methyl-1-piperazinyl)-10H-thieno[2,3-b][1,5]benzodiazepine compound may be administered as a feed additive, tablet, or transdermally.

Methods for preparing 2-methyl-4-(4-methyl-1-piperazinyl)-10H-thieno[2,3-b][1,5]benzodiazepine are provided by the '382 patent; however, the following examples may be instructive as well.

EXAMPLE 1

Technical Grade 2-methyl-4-(4-methyl-1-piperazinyl)-10H-thieno[2,3-b][1,5]benzodiazepine

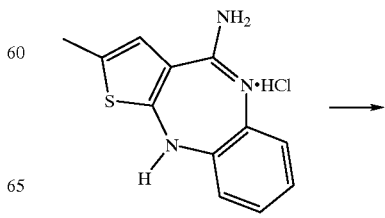

Intermediate 1

-continued

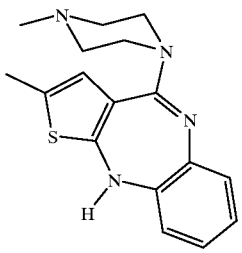

In a suitable three neck flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical 2-methyl-4-(4-methyl-1-piperazinyl)-10H-thieno[2,3-b][1,5]benzodiazepine.

Yield: 76.7%; Potency: 98.1% The procedure of Example 1 was repeated substantially as described above and provided a yield of 81% with a potency of 101.1%.

EXAMPLE 2

Technical Grade 2-methyl-4-(4-methyl-1-piperazinyl)-10H-thieno[2,3-b][1,5]benzodiazepine Intermediate 1 (supra) was suspended in DMSO (3.2 vol.) and toluene (4.5 vol.). A portion (≈0.65 vol.) of the solvent was removed by distillation at 120–125° C. The mixture was cooled to 110° C., N-methylpiperazine(NMP, 4.2 equiv.) was added and the mixture heated back to reflux (120–125° C.). Another portion (≈1 vol.) of the solvent was removed by distillation to dry the reaction mixture. A vigorous reflux was desired to drive the reaction to completion (about 7 hrs.) by removing ammonia from the reaction. The product was isolated by the slow addition of water (12.75 vol.) to the cooled (10° C.) reaction solution. The product was collected by filtration and washed with chilled water (2 vol.). The crude 2-methyl-4-(4-methyl-1-piperazinyl)-10H-thieno[2,3-b][1,5]benzodiazepine was dried in vacuo at 60° C. The product was recrystallized from hot toluene (5 vol.) to give a technical grade 2-methyl-4-(4-methyl-1-piperazinyl)-10H-thieno[2,3-b][1,5]benzodiazepine. After drying in vacuo at 50° C., the technical grade 2-methyl-4-(4-methyl-1-piperazinyl)-10H-thieno[2,3-b][1,5]benzodiazepine was recrystallized again from ethyl acetate (10 vol.)/toluene (0.62 vol.)/methanol (3.1 vol.) to give 2-methyl-4-(4-methyl-1-piperazinyl)-10H-thieno[2,3-b][1,5]benzodiazepine as a methanol solvate. The methanol solvate upon drying at >50° C. was converted to an anhydrous technical grade 2-methyl-4-(4-methyl-1-piperazinyl)-10H-thieno[2,3-b][1,5]benzodiazepine.

EXAMPLE 3

Tablet Formulation

A portion of the hydroxypropyl cellulose was dissolved in purified water to form a solution for granulation. The remaining hydroxypropyl cellulose (total of 4.0% w/w final tablet weight), which was an extra fine grade, was combined with the 2-methyl-4-(4-methyl-1-piperazinyl)-10H-thieno[2,3-b][1,5]benzodiazepine compound (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The outside powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (1.5% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. A method for treating depressive signs and symptoms in a patient not diagnosed with a psychotic condition comprising administering to said patient an effective amount of 2-methyl-4-(4-methyl-1-piperazinyl)-10H-thieno[2,3-b][1,5]benzodiazepine.

2. A method of claim 1 wherein the effective amount is from about 2.5 to about 30 mg/day for a human patient.

3. A method of claim 2 wherein the effective amount is from about 15 mg/day to about 20 mg/day.

4. A method of claim 3 wherein the 2-methyl-4-(4-methyl-1-piperazinyl)-10H-thieno[2,3-b][1,5]benzodiazepine is administered as a tablet.

5. A method of claim 1 wherein the patient is a mammal.

6. A method of claim 5 wherein the 2-methyl-4-(4-methyl-1-piperazinyl)-10H-thieno[2,3-b][1,5]benzodiazepine is administered as a feed additive.

7. A method of claim 5 wherein the patient is a human.

8. A method of claim 1 wherein 2-methyl-4-(4-methyl-1-piperazinyl)-10H-thieno[2,3-b][1,5]benzodiazepine is a pharmaceutically acceptable salt or solvate form.

9. A method for treating depression in a human not diagnosed with a psychotic condition comprising administering to said human an effective amount of 2-methyl-4-(4-methyl-1-piperazinyl)-10H-thieno[2,3-b][1,5]benzodiazepine.

10. A method of claim 9 wherein an effective amount is from about 2.5 to about 25 mg per day.

11. A method of claim 9 wherein the effective amount is from about 2.5 to about 30 mg per day.

12. A method for treating Major Depression in a mammal not diagnosed with a psychotic condition comprising administering to said mammal an effective amount of 2-methyl-4-(4-methyl-1-piperazinyl)-10H-thieno[2,3-b][1,5]benzodiazepine, or a pharmaceutically acceptable salt thereof.

13. A method of claim 12 wherein the mammal is a human.

* * * * *